United States Patent [19]

Mizushima et al.

[11] Patent Number: 4,613,505

[45] Date of Patent: Sep. 23, 1986

[54] ESTER OF FLURBIPROFEN AND EMULSION CONTAINING THE SAME

[75] Inventors: Yutaka Mizushima, Kawasaki; Katsuhiro Uchida, Kyoto; Shozoh Masumoto, Shiga; Masao Tohno, Otsu; Yoshinobu Hashimoto, Fujisawa; Kazumasa Yokoyama, Toyonaka; Hiroyuki Okamoto, Akashi; Kiichiro Nabeta, Sennan; Tadakazu Suyama, Kyoto, all of Japan

[73] Assignees: The Green Cross Corporation, Osaka; Kaken Pharmaceutical Co., Ltd., Tokyo, both of Japan

[21] Appl. No.: 622,244

[22] Filed: Jun. 19, 1984

[30] Foreign Application Priority Data

Jun. 20, 1983 [JP] Japan ................. 58-110536

[51] Int. Cl.$^4$ ................. A61K 31/235; A61K 31/685
[52] U.S. Cl. ................. 424/80; 514/533; 514/786; 514/772; 514/460; 514/473
[58] Field of Search ................. 424/279, 199; 514/533

[56] References Cited

U.S. PATENT DOCUMENTS

| | | | |
|---|---|---|---|
| 4,280,996 | 7/1981 | Okamoto et al. | 424/199 |
| 4,309,420 | 1/1982 | Ghyczy et al. | 424/199 |
| 4,411,894 | 10/1983 | Schrank et al. | 424/199 |
| 4,465,693 | 8/1984 | Strauss et al. | 424/199 |
| 4,486,417 | 12/1984 | Sugimoto et al. | 424/199 |

FOREIGN PATENT DOCUMENTS 0103265  3/1984  European Pat. Off. .

*Primary Examiner*—Stanely J. Friedman
*Attorney, Agent, or Firm*—Cushman, Darby & Cushman

[57] ABSTRACT

There is provided a fat emulsion of an ester of flurbiprofen having the formula

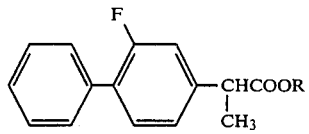

wherein R is a group of the formula

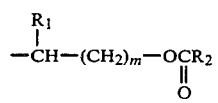

wherein $R_1$ is a hydrogen atom or a $C_1$-$C_3$ alkyl group, $R_2$ is a $C_1$-$C_{15}$ alkyl group or a $C_2$-$C_8$ alkenyl group, and m is zero or an integer of 1; or a lactone group of the formula

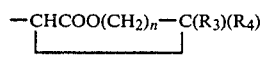

wherein $R_3$ and $R_4$ are same as or different from each other and are a hydrogen atom or a $C_1$-$C_3$ alkyl group, and n is an integer of 1 or 2.

The emulsion containing particles of a vegetable oil dissolving the ester can be orally or parenterally administered to human or animal for analgesia, antiphlogosis and antipyresis in various diseases and exhibits a high activity with small amounts in terms of flurbiprofen as compared with flurbiprofen itself.

16 Claims, 4 Drawing Figures

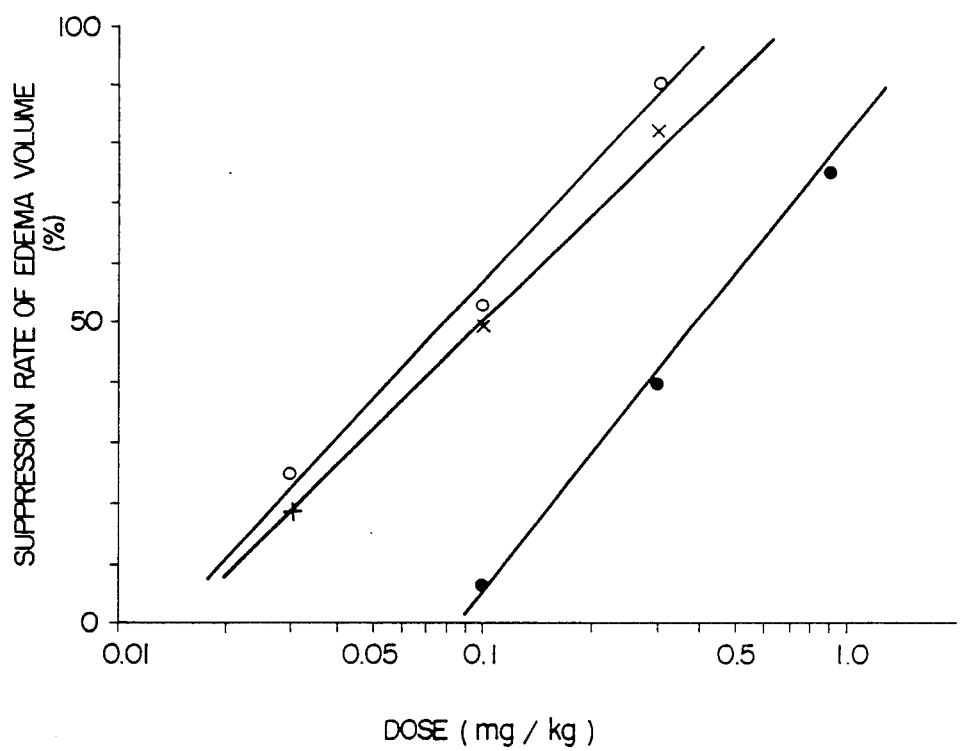
F I G. 1

ESTER OF FLURBIPROFEN AND EMULSION CONTAINING THE SAME

This invention relates to a fat emulsion of an ester of flurbiprofen [2-(2-fuloro-4-biphenylyl)propionic acid] having an antiinflammatory, an analgetic and an antipyretic activity.

It is known that 2-(2-fluoro-4-biphenylyl)propionic acid (generic name: flurbiprofen) of the formula

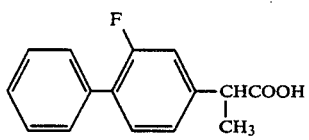

has an excellent analgetic, antiinflammatory and antipyretic activity, and is already available commercially in the form of tablets.

But flurbiprofen gives rise, when administered continually in a large amount, to gastroenteric trouble and so forth like many other non-steroidal antiphlogistics and analgesics. So, if there could be developed a preparation which would exhibit a strong and long-lasting activity in a small dose, the side effect mentioned above would be greatly reduced.

The present inventors made extensive studies to solve the problem mentioned above. As a result, there has been newly obtained a fat emulsion containing an ester of the flurbiprofen which is non-irritant, has a medicinal effect several times as large as that of flurbiprofen, and exhibits only a minor side effect.

The object of this invention is to provide an orally and parenterally administrable, particularly intravenously administrable, preparation having an excellent anti-inflammatory, analgetic and antipyretic activity and only a minor side effect.

The ester of flurbiprofen used in this invention is disclosed in European Patent Application Laid-Open No. 0103265 and has the following formula

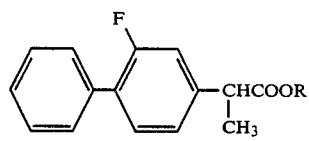 (I)

wherein R is an alkylcarbonyloxyalkyl group or an alkenylcarbonyloxyalkyl group represented by the formula (A)

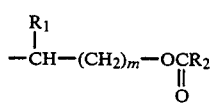

wherein $R_1$ is a hydrogen atom or a $C_1$-$C_3$ alkyl group, $R_2$ is a $C_1$-$C_{15}$ alkyl group or a $C_2$-$C_8$ alkenyl group, and m is zero or an interger of 1; or a lactone group represented by the formula (B)

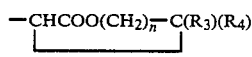 (B)

wherein $R_3$ and $R_4$ are same as or different from each other and are a hydrogen atom or a $C_1$-$C_3$ alkyl group, and n is an integer of 1 or 2.

Typical examples of the group represented by R in the general formula (I), which falls in the formula (A), include acetoxymethyl group, propionyloxymethyl group, isobutyryloxymethyl group, pivaloyloxymetyl group, palmitoyloxymethyl group, crotonoyloxymethyl group, 3,3-dimethylacryloyloxymethyl group, 1-acetoxyethyl group, 1-acetoxypropyl group, 1-propionyloxyethyl group, 1-isobutyryloxyethyl group, 1-pivaloyloxyethyl group, 1-palmitoyloxyethyl group, 1-crotonoyloxyethyl group, 1-(3,3-dimethylacryloyloxy)ethyl group, 1-(2,4-hexadienoyloxy)ethyl group, 2-acetoxyethyl group, 2-propionyloxyethyl group, 2-crotonoyloxyethyl group, 2-(3,3-dimethylacryloyloxy)ethyl group, 2-(2,4-hexadienoyloxy)ethyl group and 2-(3,7-dimethyl-2,6-octadienoyloxy)ethyl group, and which falls in the formula (B) are 3,3-dimethyl-γ-butyrolacton-2-yl group, 3,3-dimethyl-γ-valerolacton-2-yl group and 3-methyl-3-propyl-γ-butyrolacton-2-yl group.

As disclosed in European Patent Application Laid-Open No. 0103265 the flurbiprofen ester of the formula (I) mentioned above can be obtained by reacting flurbiprofen or its salt with an alkylcarbonyloxyalkyl halide or an alkenylcarbonyloxyalkyl halide represented by the general formula (II)

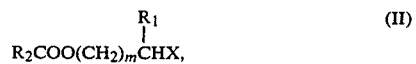 (II)

wherein $R_1$, $R_2$ and m are as defined above, X is a halogen atom including fluorine, chlorine, bromine and iodine, or with an alcohol derivative represented by the formula (III)

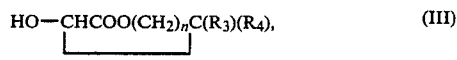 (III)

wherein $R_3$, $R_4$ and n are as defined above.

The flurbiprofen ester of the formula (I) dissolves in a vegetable oil, and the solution can easily be emulsified in the form of oil-in-water by emulsifier. The emulsion has no irritant action, and hence can be clinically applied as an intraveously administrable agent, for example. Moreover, since the emulsion is highly lipophilic, its distribution in the living body and the mode of metabolism after administration are markedly different from those in oral administration of flurbiprofen; for example it exhibits an increased drug concentration at the inflammatory site. So that, it exhibits a strong pharmacological activity and a long-lasting pharmacological effect in small doses.

Further, it is observed that the flurbiprofen ester (I) manifests the medicinal effect rapidly since it has a high decomposition rate in human articular synovia as compared with a simple ester compound of flurbiprofen such as flurbiprofen ethyl ester.

Moreover, the emulsion is low in toxicity as compared with a conventional flurbiprofen preparation; for example, the acute $LD_{50}$ value of the present preparation is twice or more that of the flurbiprofen preparation.

From the foregoing, the preparation of the present invention, as compared with the flurbiprofen preparation, is an excellent medicine which is non-irritant, excellent in its medicinal effect, both long-lasting and quick-acting, and thus has a wide safety range.

Thus, this invention provides such emulsion preparation.

The present fat emulsion preparation may be prepared by any known method using emulsifier which is physiologically acceptable. The emulsion preparation has fat particles preferably as small as possible and thus become stable against heat-sterilization and long-time storage, and is able to be administered intravenously.

Such emulsion preparation is exemplified by an emulsion which comprises preferably 0.01 to 30% (w/v) of the flurbiprofen ester (I), 5 to 50% (w/v), preferably 8 to 30% (w/v), of a vegetable oil, 1 to 50 parts, preferably 5 to 30 parts by weight of phospholipid based on 100 parts by weight of the vegetable oil, and the balance amount of an aqueous medium.

Of course, an effective amount of the flurbiprofen ester is compounded in a one-time dosage form of the preparation. Alternatively concentrated emulsion may be diluted for the purpose.

The symbol "% (w/v)" referred to in the specification and claims means the amount of a material by weight (gram) in 100 ml of the resulting emulsion.

The vegetable oil used in the invention dissolves the flurbiprofen and is emulsified in the present emulsion. The vegetable oil usable may be any edible ones such as soybean oil, cotton seed oil, sesame oil, safflower oil and corn oil, among which soybean oil is preferably used for making an emulsion capable of intravenous administration. The kind of the vegetable oils may be selected depending on the administration route of the emulsion.

The vegetable oil used in the preparation of this invention is generally a purified one having a high purity for the purpose of injection administration of the emulsion. Thus, it is preferably a purified soybean oil having a high purity (purity: 99.9% or more as total content of triglyceride and diglyceride) obtained by purifying further a purified soybean oil by, for example, steam distillation [H. J. Lips., J. Am. Oil Chemist Soc., 27, 422–423 (1950)].

The phospholipid usable in this preparation is also any origin one which is purified, for example, by a conventional method of fractionation with an organic solvent. Thus, there is mentioned, for example, a purification method according to Hanahan et al., in which 130 g of a crude egg-yolk phospholipid is dissolved in a mixture of 200 ml of cold n-hexane and 100 ml of cold acetone. Then 1170 ml of cold acetone is added gradually to the above solution with stirring. The insoluble product is recovered by filtration and then dissolved again in a mixture of 260 ml of cold n-hexane and 130 ml of cold acetone. With stirring, 1170 ml of cold acetone is added again to the solution. The insoluble product is recovered by filtration and stripped of the solvent to give 60 g of a dry product. This product contains 70 to 80% of phosphatidyl choline, 12 to 15% of phosphatidyl ethanolamine and, as other phospholipids, phosphatidyl inositol, phosphatidyl serine and sphingomyelin [D. J. Hanahan et al. J. Biol. Chem., 192, 623–628 (1951)].

The emulsion of this invention may contain further an amount of up to 0.3% (w/v) of a fatty acid having 6 to 22, preferably 12 to 20, carbon atoms or a physiologically acceptable salt thereof as an emulsifying adjuvant. It may also contain 0.5% (w/v) or less, preferably 0.1% (w/v) or less, of a cholesterol or 5% (w/v) or less, preferably 1% (w/v) or less, of phosphatidic acid as a stabilizer.

The fatty acids are either of a straight chain or of a branched chain, but straight-chained ones are preferably used. Fatty acid of natural origin are favorably used. Specific examples of preferred fatty acids and physiologically acceptable salts thereof include stearic acid, oleic acid, linolic acid, palmitic acid and linolenic acid, and an alkali metal salt such as sodium or potassium salt and an alkaline earth metal salt such as calcium salt thereof.

The cholesterol and phosphatidic acid usable as stabilizer may be any ones so long as they are usable for a medicine.

The emulsion preparation of this invention may also contain as a stabilizer a high molecular substance selected from albumin, dextran, vinyl polymer, nonionic surface active agent, gelatin and hydroxyethyl starch compounded therein. The amount of the said stabilizer to be added is 0.1 to 5 parts by weight, preferably 0.5 to 1 part by weight, based on 1 part by weight of the flurbiprofen ester.

As the albumin, when it is intended to obtain a preparation for human beings, that of human origin is preferably used because of the problem of antigenicity. As the vinyl polymer, polyvinyl pyrrolidone may be mentioned for example. As the nonionic surface active agent, there may be mentioned, for example, polyalkylene glycol, such as polyethylene glycol having an average molecular weight of 1,000 to 10,000, preferably 4,000 to 6,000; poloxyalkylene copolymer such as polyoxyethylene/polyoxypropylene copolymer having an average molecular weight of 1,000 to 20,000, preferably 6,000 to 10,000; hardened castor oil polyoxyalkylene derivative such as hardened castor oil-polyoxyehtylene-(40)-ether, -(20)-ether, or -(100)-ether; and castor oil polyoxyalkylene derivative such as castor oil-polyoxyethylene-(40)-ether, -(100)-ether or -(20)-ether.

It is also possible to add a conventional isotonifying agent such as glycerol and glucose for isotonification of the emulsion. The aqueous medium used may be distilled water, and preferably phosphate or citrate buffer solution (pH 6–8).

The emulsion of this invention is prepared, for example, by the following process.

Thus, predetermined amounts of flurbiprofen ester (I), phospholipid, and, if necessary, the above-mentioned additives are mixed with a required amount of soybean oil, and the mixture is heated at 40° to 70° C. to form a solution. A required amount of an aqueous medium is added to the solution, and the mixture is emlusified at 20° to 80° C. by means of a conventional mixer (for example Homomixer) to give a crude emulsion. Stabilizers and isotonifying agents may be added at this stage.

The crude emulsion is then homogenized at 20° to 80° C. by using a homogenizer (for example, a pressure-jet type homogenizer such as Manton-Gaulin type homogenizer or an ultrasonic homogenizer) to obtain a homogenized, extremely fine fat emulsion containing the flurbiprofen ester, which can be administered by intravenous injection. The emulsion has an average particle diameter of 1.0 μm or less and has an excellent stability against heat-sterilization and storage.

When a Manton-Gualin type homogenizer is used as the homogenizer, for example, the homogenization of crude emulsion is carried out, for example, passing the crude emulsion through the said homogenizer 0 to 2 times at the first-stage pressure of 100 to 150 kg/cm² to form a crude emulsion, and then 5 to 15 times under the second pressure of 400 to 700 kg/cm².

The dose of the emulsion of this invention varies depending upon administration route, dosage form, symptoms, and so forth. For adults, for example, when the emulsion is administered intravenously, the dose is generally 0.1 to 500 ml/time. The dose in terms of the flurbiprofen ester contained in the emulsion is generally 0.5 to 200 mg/time for an adult.

The preparation of this invention exhibits a high activity with a small amount of the present flurbiprofen ester administered, and the activity is retained for a long time. It is used for analgesia, antiphlogosis and antipyresis in such diseases as rheumatoid arthritis, spondylosis deformans, lumbago, gouty ictus, scapular periarthritis, pharyngolaryngitis, acute otitis media, neurodynia, cystitis, prostatitis, toothache, inflammation and pain following tooth extraction, inflammation, swelling and pain following operation or tauma, osteoarthritis, acute fervescence caused by superior respiratory tract inflammation etc., headache, tendovaginitis, menorrhalgia and various kind or carcinomatous pain.

This invention will be illustrated in more detail below with reference to Examples and Experimental Examples, but it is not limited thereto.

In the Examples disclosing detailed preparation of the present emulsion, the resulting emulsions were tolerable against heat-sterilization and stable at least for 24 months at room temperature. The emulsions are capable of intravenous administration.

Drawing shows the characteristic properties determined in the Experimental Examples and, FIG. 1 is a graph showing the anti-inflammatory action of the emulsion of this invention as determined according to the carrageenin edema method;

Figure 2:
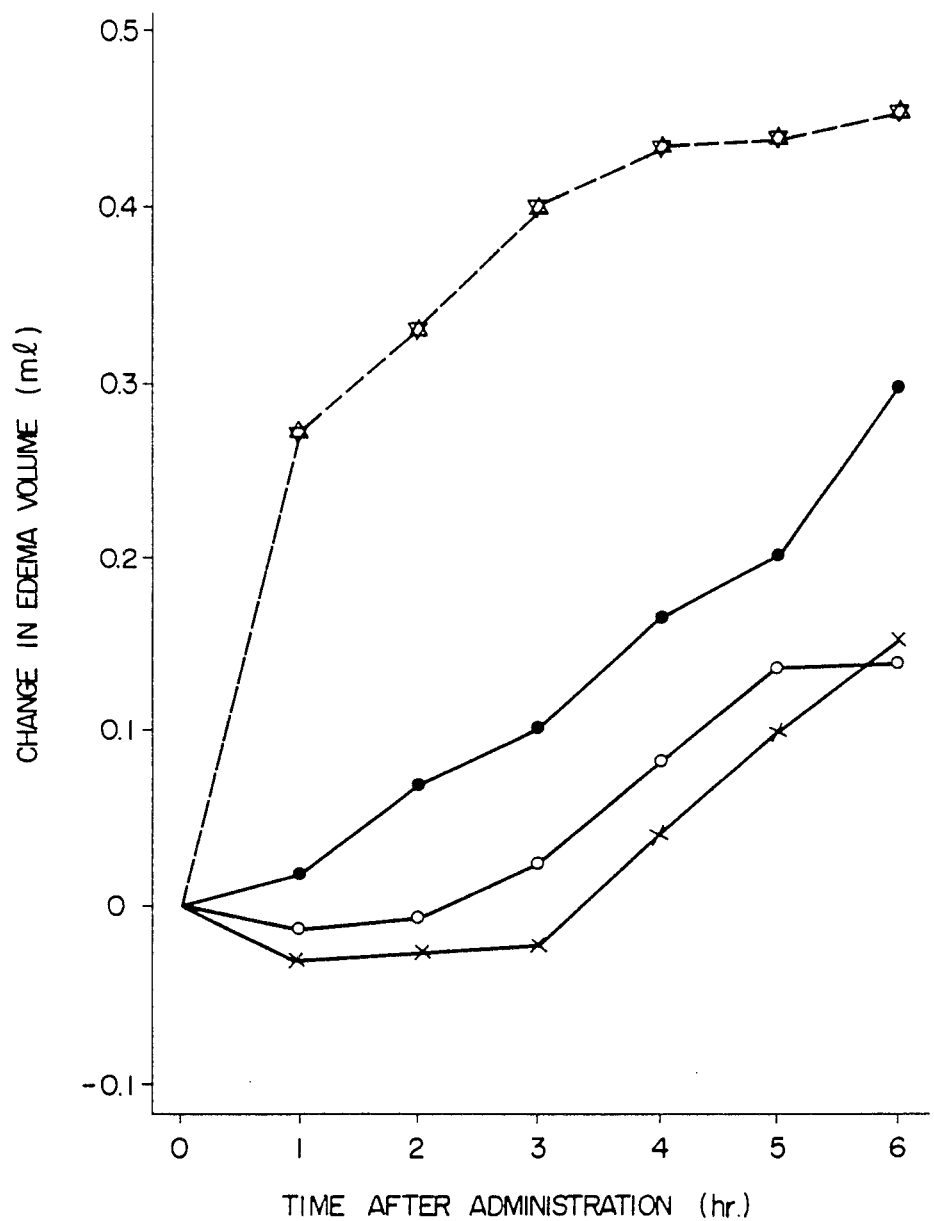
FIG. 2 is a graph showing the durability of anti-inflammatory action of the emulsion of this invention as determined according to the carrageenin edema method.

In the graphs, a black dot indicates the physiological saline solution of flurbiprofen (sodium salt); a white dot indicates the acetoxymethyl 2-(2-fluoro-4-biphenylyl)-propionate fat emulsion; an x indicates the 1-acetoxyethyl 2-(2-fluoro-4-biphenylyl)propionate fat emulsion; and a white star mark indicates the physiological saline itself as a control.

Reference Example 1

Method of preparing a flurbiprofen ester

Into a solution of 7.32 g (30 mmol) of 2-(2-fluoro-4-biphenylyl)propionic acid in 100 ml of anhydrous dimethylformamide, was added with ice-cooling 2.1 g (15 mmol) of anhydrous potassium carbonate, and the mixture was stirred for 1 hour. To the above mixture was added dropwise in the course of 10 minutes at 0° to 5° C. 3.3 g (30 mmol) of acetoxymethyl chloride which had been purified by distillation. After completion of the addition, the mixture was stirred for 2 hours at room temperature. The reaction mixture was cooled with ice, filtered to remove the inorganic materials, and then the solvent was distilled off under reduced pressure. The residue was mixed with 150 ml of diethyl ether, washed successively with water, 10% aqueous sodium carbonate solution and saturated aqueous sodium chloride solution. The organic layer was dried over anhydrous magnesium sulfate, and the solvent was distilled off under reduced pressure to give 8.24 g of an oily crude product in 86.9% crude yield.

The product was further subjected to vacuum distillation under a nitrogen atmosphere to give 6.55 g of oily acetoxymethyl 2-(2-fluoro-4-biphenylyl)propionate. Yield: 69.1%, b.p.: 196°–197° C./0.4 mmHg In the same manner as above, the flurbiprofen esters listed in Table 1 were prepared.

TABLE 1

| No. | Substituent R in formula (I) | b.p. (°C./mmHg) |
|---|---|---|
| 2 | Propionyloxymethyl | 195–196/0.8 |
| 3 | Isobutyryloxymethyl | 188–190/0.4 |
| 4 | Crotonoyloxymethyl | 217–219/0.4 |
| 5 | 3,3-Dimethylacryloyloxymethyl | 210–214/0.5 |
| 6 | Palmitoyloxymethyl | 45.5–48.0 (m.p.) |
| 7 | Pivaloyloxymethyl | 191–194/0.4 |
| 8 | 1-Acetoxyethyl | 173–174/0.8 |
| 9 | 1-Propionyloxyethyl | 188–191/0.4 |
| 10 | 1-Isobutyryloxyethyl | 160–164/0.5 |
| 11 | 1-Pivaloyloxyethyl | 166–172/0.55 |
| 12 | 1-Palmitoyloxyethyl | >200/0.5 |
| 13 | 1-Acetoxypropyl | >150/0.5 |
| 14 | 1-Crotonoyloxyethyl | 195–197/0.3 |
| 15 | 1-(3,3-Dimethylacryloyloxy)-ethyl | 194/0.6 |
| 16 | 1-(2,4-Hexadienoyloxy)ethyl | >200/0.5 |
| 17 | 2-Acetoxyethyl | 234–238/1 |
| 18 | 2-Propionyloxyethyl | 225–228/0.5 |
| 19 | 2-Crotonoyloxyethyl | 205–215/1.5 |
| 20 | 2-(3,3-Dimethylacryloyloxy)-ethyl | 225–228/0.8 |
| 21 | 2-(2,4-Hexadienoyloxy)ethyl | 59.0–61.0 (m.p.) |
| 22 | 2-(3,7-Dimethyl-2,6-octadienoyloxy)ethyl | >250/1 |

Reference Example 2

In 40 ml of anhydrous dichloromethane were dissolved 2.44 g (10 mmoles) of 2-(2-fluoro-4-biphenylyl)-propionic acid, 1.3 g (10 mmols) of 2-hydroxy-3,3-dimethylbutyrolactone and 0.1 g of p-dimethylaminopyridine. To the resulting solution was added dropwise 2.0 g (10 mmoles) of dicyclohexylcarbodiimide, and the resulting reaction mixture was stirred at a room temperature for one hour. After completion of the reaction, the reaction mixture was cooled to a temperature of 0° C., and the precipitated dicyclohexylurea was filtered off. The resulting filtrate was washed successively with 0.1N hydrochloric acid, a saturated sodium bicarbonate solution and a saturated sodium chloride solution, and then the organic layer was dried with anhydrous magnesium sulfate. After distilling away the solvent under reduced pressure, the resulting light yellowish liquor was distilled under reduced pressure for purification to give 2.41 g (yield: 68%) of the desired compound, oily 3,3-Dimethyl-2-[2-(2-fluoro-4-biphenylyl)propionyloxy]-γ-butyrolactone having a boiling point of 198° to 209° C./0.9 mmHg.

Example 1

To 30 g of purified soybean oil were added 3.6 g of phospholipid, 6 g of acetoxymethyl 2-(2-fluoro-4-biphenylyl)propionate, 0.15 g of sodium oleate and 0.15 g of phosphatidic acid, and the mixture was heated at 40° to 75° C. to form a solution. The solution was mixed with 200 ml of distilled water and then 7.5 g of glycerol (Japanese Pharmacopoeia), made up into a total volume of 300 ml with distilled water for injection of 20° to 40° C., and then treated with a Homomixer to form a crude emulsion.

The crude emulsion was then emulsified by passing it through a Manton-Gaulin type homogenizer under pressure of 120 kg/cm² in the first stage and 10 times under total pressure of 500 kg/cm². Thus, a homogenized, extremely fine fat emulsion was obtained. The emulsion had an average particle diameter of 0.2 to 0.4 μm and contained no particle larger than 1 μm.

Example 2

The procedures in Example 1 were repeated except that 1-acetoxyethyl 2-(2-fluoro-4-biphenylyl)propionate was used in place of acetoxymethyl 2-(2-fluoro-4-biphenylyl)propionate.

A homogenized, extremely fine fat emulsion was obtained. The emulsion had an average particle diameter of 0.2 to 0.4 μm and contained no particle larger than 1 μm.

Example 3

To 30 g of purified soybean oil were added 3.6 g of phospholipid, 3 g of 2-acetoxyethyl 2-(2-fluoro-4-biphenylyl)propionate, 0.15 g of sodium oleate, and 0.15 g of cholesterol, and the mixture was heated at 40° to 75° C. to form a solution. The solution was mixed with 200 ml of distilled water and then 7.5 g of glycerol (Japanese Pharmacopoeia), made up into a total volume of 300 ml with distilled water for injection of 20° to 40° C., and then treated with Homomixer to form a crude emulsion.

The crude emulsion was then emulsified by passing it through a Manton-Gaulin type homogenizer under pressure of 120 Kg/cm² in the first stage and 10 times at 500 Kg/cm² in total pressure. A homogenized, extremely fine fat emulsion was thus obtained. The emulsion had an average particle size of 0.2 to 0.4 μm and contained no particle larger than 1 μm.

Example 4

To 30 g of purified soybean oil were added 3.6 g of phospholipid, 3 g of pivaloyloxymethyl 2-(2-fluoro-4-biphenylyl)propionate, 0.15 g of sodium oleate and 0.15 g of cholesterol, and the mixture was heated at 40° to 75° C. to form a solution. The solution was mixed with 200 ml of distilled water and then 7.5 g of glycerol (Japanese Pharmacopoeia), made up into a total volume of 300 ml with distilled water for injection of 20° to 40° C., and then treated with Homomixer to form a crude emulsion.

The crude emulsion was then emulsified by passing it through a Manton-Gaulin type homogenizer under pressure of 120 Kg/cm² in the first stage and 10 times at 500 Kg/cm² in total pressure. Thus, a homogenized, extremely fine fat emulsion was obtained. The emulsion had an average particle diameter of 0.2 to 0.4 μm and contained no particle larger than 1 μm.

Example 5

To 90 g of purified soybean oil were added 3.6 g of phospholipid, 3 g of crotonoyloxymethyl 2-(2-fluoro-4-biphenylyl)propionate, 0.15 g of sodium oleate and 0.15 g of phosphatidic acid, and the mixture was heated at 40° to 75° C. to form a solution. The solution was mixed with 200 ml of distilled water and then 7.5 g of glycerol (Japanese Pharmacopeia), made up into a total volume of 300 ml, and treated with Homomixer to form a crude emulsion.

The crude emulsion was then emulsified by passing it through a Manton-Gaulin type homogenizer under pressure of 120 Kg/cm² in the first stage and ten times at 500 Kg/cm² in total pressure. Thus, a homogenized, extremely fine fat emulsion was obtained. The emulsion had an average particle diameter of 0.2 to 0.4 μm and contained no particle large than 1 μm.

Example 6

To 30 g of purified soybean oil were added 3.6 g of phospholipid, 1.5 g of palmitoyloxymethyl 2-(2-fluoro-4-biphenylyl)propionate, 0.15 g of sodium oleate and 0.15 g of phosphatidic acid, and the mixture was heated at 40° to 75° C. to form a solution. The solution was mixed with 200 ml of distilled water and then 7.5 g of glycerol (Japanese Pharmacopoeia), made up into a total volume of 300 ml with distilled water for injection of 20° to 40° C., and treated with Homomixer to form a crude emulsion.

The crude emulsion was then emulsified by passing it through a Manton-Gaulin type homogenizer under pressure of 120 Kg/cm² in the first stage and ten times at 500 Kg/cm² in total pressure. Thus, a homogenized, extremely fine fat emulsion was obtained. The emulsion had an average particle diameter of 0.2 to 0.4 μm and contained no particle larger than 1 μm.

Example 7

To 30 g of purified soybean oil were added 3.6 g of phospholipid, 1.5 g of 3,3-dimethyl-γ-butyrolacton-2-yl 2-(2-fluoro-4-biphenylyl)propionate, 0.15 g of sodium oleate, 0.15 g of phosphatidic acid and 900 μg of albumin, and the mixture was heated at 40° to 75° C. to form a solution. The solution was mixed with 200 ml of distilled water and then 7.5 g of glycerol (Japanese Pharmacopeia), made up into a total volume of 300 ml, and treated with Homomixer to form a crude emulsion.

The crude emulsion was then emulsified by passing it through a Manton-Gaulin type homogenizer under pressure of 120 Kg/cm² in the first stage and ten times at 500 Kg/cm² in total pressure. Thus, a homogenized, extremely fine fat emulsion was obtained. The emulsion had an average particle diameter of 0.2 to 0.4 μm and contained no particle larger than 1 μm.

Example 8

To 30 g of purified soybean oil were added 3.6 g of phospholipid and 6 g of acetoxymethyl 2-(2-fluoro-4-biphenylyl)propionate, and the mixture was heated at 40° to 75° C. to form a solution. The solution was mixed with 200 ml of a buffer solution (phosphate and citrate, pH 7.0) and then 7.5 g of glycerol (Japanese Pharmacopoeia), made up into a total volume of 300 ml with the said buffer solution at 20° to 40° C., and then treated with Homomixer to form a crude emulsion.

The crude emulsion was then emulsified by passing it through a Manton-Gaulin type homogenizer under pressure of 120 Kg/cm² in the first stage and 10 times at 500 Kg/cm² in total pressure. Thus, a homogenized, extremely fine fat emulsion was obtained. The emulsion had an average particle diameter of 0.2 to 0.4 μm and contained no particle larger than 1 μm.

Experimental Example 1

Acute toxicity

Male, ddY-strain mice, weighing 20 to 22 g and at 6 weeks of age, were used to determine $LD_{50}$ of the preparation of this invention (Examples 1 or 2) and of a physiological saline preparation of flurbiprofen sodium salt as the control. The value of $LD_{50}$ was determined by administering each of the test preparations intravenously or orally and calculating from the mortality observed after one week.

The results obtained are as shown in Table 2.

TABLE 2

| Test preparation | $LD_{50}$ (mg/Kg) in terms of flurbiprofen | |
|---|---|---|
| | Intravenous administration | Oral administration |
| Acetoxymethyl 2-(2-fluoro-4-biphenylyl)-propionate in emulsion | 500 or more | 800 |
| 1-Acetoxyethyl 2-2-fluoro-4-biphenylyl)-propionate in emulsion | 500 or more | 800 |
| Flurbiprofen sodium salt in physiological saline preparation | 220 | 400 |

It can be seen from Table 2 that the toxicity of the fat emulsion of this invention was reduced to ½ or less of that of the control preparation.

Experimental Example 2

Anti-inflammatory action and its durability

Male, Wistar-strain rats, weighing 140 to 160 g and at 7 weeks of age, were used and injected subcutaneously at the left hind paw 0.1 ml of a 1% carrageenin solution in physiological saline to form an edema. Two hours after, they were administered through the tail vein varied amounts of 0.03 mg/Kg, 0.1 mg/Kg and 0.3 mg/Kg in terms of flurbiprofen as shown in FIG. 1 of acetoxymethyl flurbiprofen ester and acetoxyethyl flurbiprofen ester, respectively, contained in the present emulsions which were each prepared in Examples 1 and 2, and diluted to concentrations of 0.03 mg/ml, 0.10 mg/ml and 0.3 mg/ml, as well as 0.1 mg/Kg, 0.3 mg/Kg and 1.0 mg/Kg as acid of flurbiprofen sodium salt contained in physiological saline as a control.

For evaluation of edema suppression effect, the suppression rate (%) of edema volume after 2 hours from the administration of the preparation was determined on the basis of the edema volume of 2 hours after the injection of carrageenin.

The results are as shown in FIG. 1.

Further, the change in edema volume formed by similar way and after the similar administration of the preparation was determined. In this case the dose of the preparation was 0.5 mg/Kg of flurbiprofen in the control and same amount in terms of flurbiprofen in the flurbiprofen ester emulsions. The determination was carried out every one hour to the point of time 6 hours after the administration of the preparation to evaluate the durability of the activity. Besides the flurbiprofen control, a mere saline water was added in this case as another control.

The results are as shown in FIG. 2.

As shown in FIG. 1, it is observed that the emulsion of this invention suppresses the carrageenin edema by 50% at a dose of 0.08 to 0.1 mg/Kg (calculated in terms of flurbiprofen), thus exhibiting an anti-inflammatory action 4 to 5 times as strong as that of the control preparation whose corresponding dose is 0.4 mg/Kg.

Further, as shown in FIG. 2, it is observed that the emulsion of this invention exhibits more durable anti-inflammatory action as compared with the control preparations.

Experimental Example 3

Analgetic action

Figure 3:
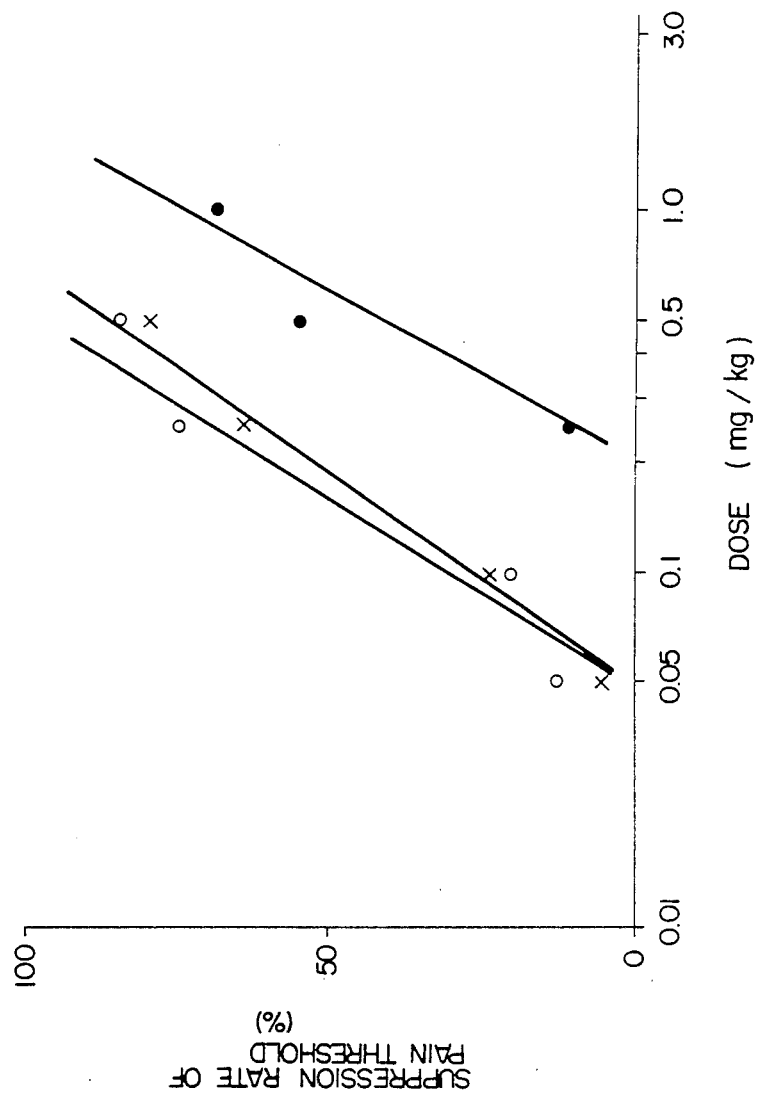
FIG. 3 is a graph showing the analgetic action of the emulsion of this invention as determined according to the Randall-Selitto method.

Male, Wistar-strain rats weighing 120 to 150 g were injected subcutaneously at the right hind paw 0.1 ml of 1% carrageenin solution in physiological saline. After 2 hours, the pressure-stimulus pain thresholds at the inflamed paw and the non-inflamed paw were determined by means of an instrument for measuring pressure-stimulus analgetic effect (UGO BASIL). Then the present emulsion preparations containing same flurbiprofen esters as in Experimental Example 2 of this invention and a physiological saline preparation of flurbiprofen sodium salt as a control were administered in varied amounts in termes of flurbiprofen as shown in FIG. 3 through the tail vein. At points of time 1, 2 and 3 hours after administration of the test preparation, the pressure-stimulus pain thresholds at the inflamed paw and the non-inflamed paw were determined in a similar manner.

The pain coefficient according to the Randall-Selitto's method was determined as the sum of the values obtained at each time by subtracting the threshold value at the inflamed paw from that at the non-inflamed paw.

Suppression rates were determined from the comparison of the pain coefficient of each of the test preparation groups with that of the control group to evaluate the analgetic action.

The results are as shown in FIG. 3.

It is observed from FIG. 3 that the fat emulsion of this invention suppresses the pressure-stimulus pain threshold by 50% at a dose of 0.16 to 0.19 mg/Kg (calculated in terms of flurbiprofen), thus exhibiting an analgetic action about 3 to 4 times as strong as that of the control group, whose corresponding dose is 0.6 mg/Kg.

Experimental Example 4

Antipyretic action

Male, Wistar-strain rats weighing 140 to 160 g were used. Two milliliters of a 20% yeast suspension in physiological saline was injected subcutaneously at the back of the rats that had shown a normal body temperature on the day before the experiment. The rats which showed a temperature rise to 39° C. or higher after 18 hours were selected and divided into equal groups. After measuring the body temperature before administration, the emulsion preparation containing same flurbiprofen esters as in Experimental Example 2 of the invention and a physiological saline solution of flurbiprofen sodium salt as a control were administered in varied amounts in terms of flurbiprofen to the selected animals through the tail vein. Body temperatures were measured 1, 2, 3 and 4 hours after administration. In each of the administration groups, the lowered body temperature at the time when a maximum antipyretic effect was exhibited was compared with the temperature at the time of fervescence to determine the fervescence suppression rate.

Figure 4:
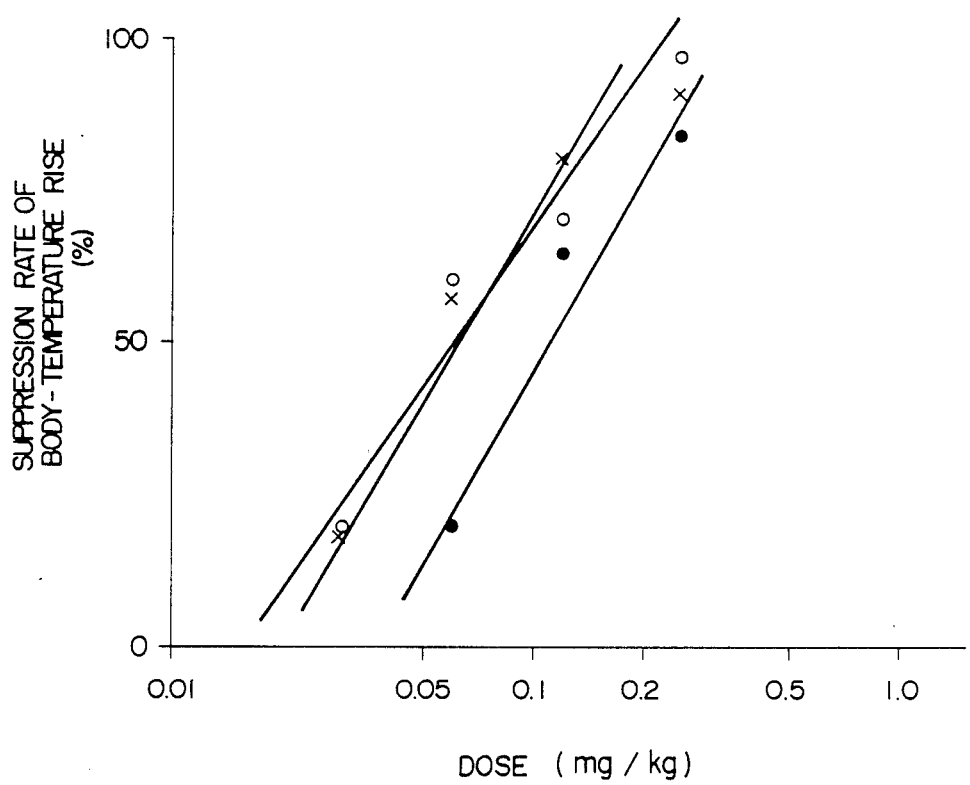
FIG. 4 is a graph showing the antipyretic action of the emulsion of this invention as determined according to the yeast feverescene method.

The results are as shown in FIG. 4.

It can be observed from FIG. 4 that the emulsion of this invention suppresses the rise of body temperature by 50% at a dose of about 0.06 mg/Kg (calculated in terms of flurbiprofen), thus exhibiting an antipyretic action about twice as strong as the control preparation whose corresponding dose is 0.11 mg/Kg.

Experimental Example 5

Distribution into the inflammation site

Male, Wistar-strain rats, weighing 123 to 147 g and at 7 weeks of age, were injected subcutaneously at the hind paw 0.1 ml of 1% carrageenin solution in physiological saline. After 1 hour, the emulsion preparation containing 1-acetoxyethyl flurbiprofen ester of this invention prepared in Example 2 was intravenously administered at a dose of 1 mg/Kg. On the other hand, a gum arabic suspension of flurbiprofen was orally administered to the animal at a dose of 0.74 mg/Kg (equimolar dose). At 0.5 and 1 hour after the administration of the test preparation, the animal was bled out under anesthesia to death and the edema part was excised. The concentration of flurbiprofen in the edema was then determined by high-performance liquid chromatography.

The results are as shown in Table 3.

TABLE 3

| Test preparation (Administration route) | Flurbiprofen concentration (μg/g) | |
|---|---|---|
| | After 0.5 hr | After 1 hr |
| 1-Acetoxyethyl 2-(2-fluoro-4-biphenylyl)-propionate in emulsion (Intravenously) | 1.26 ± 0.488 | 1.11 ± 0.083 |
| Flurbiprofen in gum arabic suspension (Orally) | 0.20 ± 0.076 | 0.26 ± 0.053 |

Note: Each value indicates the mean value ± standard error of 4 animals.

As shown in Table 3, it can be observed that the fat emulsion of this invention (administered intravenously) exhibits a local concentration of the drug 4 to 6 times as high as that of the control preparation (administered orally).

Experimental Example 6

Hydrolysis in human articular synovia

Into 1 ml of articular synovia of a patient with rheumatoid or osteoarthritis, was added 10 ml of an acetone solution of ethyl 2-(2-fluoro-4-biphenylyl)propionate(ethyl flurbiprofen ester: compound 1) or acetoxymethyl 2-(2-fluoro-4-biphenylyl)propionate(acetoxymethyl flurbiprofen ester; compound 2) (each being contained in an equimolar amount to 50 ng of flurbiprofen), respectively, and the mixture was incubated for 60 minutes at 37° C. The concentration of flurbiprofen formed by hydrolysis was then determined by gas chromatography.

The results are as shown in Table 4.

TABLE 4

| Patient (Disease, sex, age) | Hydrolysis rate (%) | |
|---|---|---|
| | Compound 1 | Compound 2 |
| K.A. (Osteoarthritis, female, 68) | 0.0 | 64.7 |
| E.M. (Rheumatoid, female, 51) | 0.0 | 64.1 |
| R.H. (Rheumatoid, female, 23) | 0.0 | 65.7 |
| K.T. (Rheumatoid, female, 67) | 25.8 | 91.3 |
| K.M. | 2.0 | 84.4 |

TABLE 4-continued

| Patient (Disease, sex, age) | Hydrolysis rate (%) | |
|---|---|---|
| | Compound 1 | Compound 2 |
| (Unknown, female, 34) | | |

As shown in Table 4, it can be observed that acetoxymethyl 2-(2-fluoro-4-biphenylyl)propionate (compound 2) to be contained in the preparation of this invention is effectively hydrolyzed in human articular synovia to liberate the physiologically active substance, flurbiprofen, while ethyl 2-(2-fluoro-4-biphenylyl)propionate (compound 1) which is a simple ester, is substantially not hydrolyzed.

What is claimed is:

1. An intravenously injectable pharmaceutical emulsion comprising a physiologically acceptable phospholipid emulsifier and particles of soybean oil which contain an effective amount of at least one ester of flurbiprofen of the formula

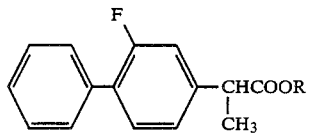

wherein R is a group of the formula

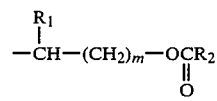

wherein $R_1$ is a hydrogen atom or a $C_1$–$C_3$ alkyl group, $R_2$ is a $C_1$–$C_{15}$ alkyl group or a $C_2$–$C_8$ alkenyl group, and m is zero or an integer of 1; or a lactone group of the formula

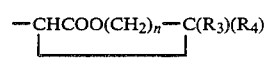

wherein $R_3$ and $R_4$ are same as or different from each other and are a hydrogen atom or a $C_1$–$C_3$ alkyl group, and n is an integer of 1 or 2; and an aqueous medium.

2. A pharmaceutical emulsion of claim 1 wherein the vegetable oil is soybean oil.

3. A pharmaceutical emulsion of claim 1 wherein an effective amount as an emulsifying adjuvant of a fatty acid having 6 to 22 carbon atoms or a physiologically acceptable salt thereof is also included.

4. A pharmaceutical emulsion of claim 1 wherein a stabilizing amount of cholesterol, phosphatidic acid or mixture thereof is further contained as a stabilizer.

5. A pharmaceutical emulsion of claim 1 wherein a stabilizing amount of an albumin, a dextran, a polyvinyl pyrrolidone, a polyalkylene glycol having a molecular weight of 1,000 to 10,000, a polyoxyethylene-polyoxypropylene copolymer having a molecular weight of 1,000 to 20,000, a hardened or not hardened caster oil-polyoxyalkylene ether, gelatin or hydroxyethylstarch is also included.

6. A pharmaceutical emulsion of claim 1 wherein an isotonifying amount of glycerol and/or glucose is further contained.

7. A pharmaceutical emulsion of claim 1, which comprises 5 to 50% (w/v) of soybean oil dissolving 0.01 to 30% (w/v) based on the emulsion of the ester of flurbiprofen, 1 to 50 parts by weight based on 100 parts by weight of the soybean oil, of phospholipid, and the balance an aqueous medium.

8. A pharmaceutical emulsion of claim 7 wherein 0.3% (w/v) or less of a fatty acid having 6 to 22 carbon atoms or a physiologically acceptable salt thereof and 0.1% (w/v) or less of a cholesterol or 0.5% (w/v) or less of phosphatidic acid are further contained.

9. A pharmaceutical emulsion of claim 7 wherein the aqueous medium is of phosphate and/or citrate buffer solution having a pH in the range of of 6-8 inclusive.

10. A pharmaceutical emulsion of claim 1, wherein the ester of flurbiprofen is selected from the group consisting of acetoxymethyl, propionyloxymethyl, isobutyryloxymethyl, crotonoyloxymethyl, 3,3-dimethylacryloyloxymethyl, palmitoyloxymethyl, pivaloyloxymethyl, 1-acetoxyethyl, 1-propionyloxyethyl, 1-isobutyryloxyethyl, 1-pivaloyloxyethyl, 1-palmitoyloxyethyl, 1-acetoxypropyl, 1-crotonoyloxyethyl, 1-(3,3-dimethylacryloyloxy)ethyl, 1-(2,4-hexadienoyloxy)ethyl, 2-acetoxyethyl, 2-propionyloxyethyl, 2-crotonoyloxyethyl, 2-(3,3-dimethylacryloyloxy)ethyl, 2-(2,4-hexadienoyloxy)ethyl, 2-3,7-dimethyl-2,6-octadienoyloxy)ethyl and 3,3-dimethyl-γ-butyrolacton-2yl esters of flurbiprofen.

11. A pharmaceutical emulsion of claim 10, wherein the ester of flurbiprofen is selected from the group consisting of acetoxymethyl, crotonoyloxymethyl, palmitoyloxymethyl, pivaloyloxymethyl, 1-acetoxyethyl, 2-acetoxyethyl and 3,3-dimethyl-γ-butyrolacton-2-yl esters of flurbiprofen.

12. A pharmaceutical emulsion of claim 10, wherein the ester of flurbiprofen is selected from the group consisting of acetoxymethyl and 1-acetoxyethyl esters of flurbiprofen.

13. A method of treating a mammal suffering inflammation, pain or fever, which comprises administering to the mammal an effective amount of the emulsion of claim 1.

14. A method according to claim 13, wherein the emulsion contains at least one ester of flurbiprofen selected from the group consisting of acetoxymethyl, propionyloxymethyl, isobutyryloxymethyl, crotonoyloxymethyl, 3,3-dimethylacryloyloxymethyl, palmitoyloxymethyl, pivaloyloxymethyl, 1-acetoxyethyl, 1-propionyloxyethyl, 1-isobutyryloxyethyl, 1-pivaloyloxyethyl, 1-palmitoyloxyethyl, 1-acetoxypropyl, 1-crotonoyloxyethyl, 1-(3,3-dimethylacryloyloxy)ethyl, 1-(2,4-hexadienoyloxy)ethyl, 2-acetoxyethyl, 2-propionyloxyethyl, 2-crotonoyloxyethyl, 2-(3,3-dimethylacryloyloxy)ethyl, 2-(2,4-hexadienoyloxy)ethyl, 2-3,7-dimethyl-2,6-octadienoyloxy)ethyl and 3,3-dimethyl-γ-butyrolacton-2yl esters of flurbiprofen.

15. A method according to claim 14, wherein the ester is selected from the group consisting of acetoxymethyl, crotonoyloxymethyl, palmitoyloxymethyl, pivaloyloxymethyl, 1-acetoxyethyl, 2-acetoxyethyl and 3,3-dimethyl-γ-butyrolacton-2-yl esters of flurbiprofen.

16. A method according to claim 13, wherein the ester of flurbiprofen is selected from the group consisting of acetoxymethyl and 1-acetoxyethyl esters of fluribiprofen.

* * * * *